US007770577B2

(12) United States Patent
Conner

(10) Patent No.: US 7,770,577 B2
(45) Date of Patent: *Aug. 10, 2010

(54) METHODS AND DEVICES FOR TREATING LUNG DYSFUNCTION

(76) Inventor: Gregory E Conner, Department of Cell Biology, R-124, University of Miami School of Medicine, P.O. Box 016960, Miami, FL (US) 33101

(*) Notice: Subject to any disclaimer, the term of this patent is extended or adjusted under 35 U.S.C. 154(b) by 893 days.

This patent is subject to a terminal disclaimer.

(21) Appl. No.: 10/771,057

(22) Filed: Feb. 3, 2004

(65) Prior Publication Data

US 2004/0156917 A1    Aug. 12, 2004

Related U.S. Application Data

(63) Continuation of application No. 10/146,405, filed on May 14, 2002, now Pat. No. 6,702,998.

(60) Provisional application No. 60/291,210, filed on May 15, 2001.

(51) Int. Cl.
*A61M 11/00* (2006.01)
*A61K 33/40* (2006.01)
*A61K 31/075* (2006.01)

(52) U.S. Cl. .................. 128/200.14; 424/616; 514/714

(58) Field of Classification Search ............ 128/200.14; 424/616; 514/714
See application file for complete search history.

(56) References Cited

U.S. PATENT DOCUMENTS

| 4,667,668 | A | * | 5/1987 | Wetterlin ............... 128/203.15 |
| 5,503,853 | A | | 4/1996 | Bollen et al. |
| 6,056,169 | A | * | 5/2000 | Bruna et al. ................. 222/636 |
| 6,149,908 | A | | 11/2000 | Claesson et al. |
| 6,207,703 | B1 | * | 3/2001 | Ponikau ....................... 514/460 |
| 6,223,746 | B1 | | 5/2001 | Jewett et al. |
| 6,589,481 | B1 | * | 7/2003 | Lin et al. ....................... 422/33 |
| 2004/0028749 | A1 | | 2/2004 | Slungaard |

OTHER PUBLICATIONS

Reiter et al. "Nonspecific Bacterial Activity of the Lactoperoxidase-Thiocyanate-Hydrogen Peroxide System of Milk Against *Escherichia coli* and Some Gram-Negative Pathogens," Infection and Immunity, Mar. 1976, pp. 800-807.*
Wijkstrom-Frei et al. "Lactoperoxidase and Human Airway Host Defense," Am. J. Respir. Cell Mol. Biol. 2003, 29, pp. 206-212.*
Conner et al. "The Lactoperoxidase system links anion transport to host defense in cystic fibrosis," FEBS letters 2007, 581, pp. 271-278.*
MSDS for potassium thiocyanate -accessed on Jul. 10, 2008 at http://www.jtbaker/msds/englishhtml/p6181.htm.*
MSDS for 3% aqueous hydrogen peroxide -accessed on Jul. 10, 2008 at http://www.jtbaker/msds/englishhtml/h4070.htm.*
MSDS for 30% aqueous hydrogen peroxide -accessed on Jul. 10, 2008 at http://www.bu.edu/es/labsafety/ESMSDSs/MSHydPeroxide.html.*
Ashdown et al. "Hydrogen Peroxide Poisoning: Causing Brain Infarction: Neuroimaging Findings," A.J.R. Jun. 1998, 170, pp. 1653-1655.*
Watt et al. "Hydrogen peroxide poisoning," Toxicol. Rev. 2004, 23(1), Abstract only.*
Medical Toxicology Unit, International Programme on Chemical Safety Poisons Information Monograph 946: Chemical-accessed Jul. 11, 2008 at http://www.inchem.org/documents/pims/chemical/pim946.htm.*
Ciencewicki et al. Journal of Allergy and Clinical Immunology, 2008, 122(3), pp. 456-468 (printout pp. 1-58).*
Pelaia et al. J. Cell Biochem 2004, 93(1), pp. 142-152 (abstract only).*
Kim et al. Exp. Mol. Med. 2008, 40(3), pp. 320-331 (abstract only).*
Online description and quotation from Mr. Bill Munro concerning his prior use of an inhaler comprising hydrogen peroxide: www.earthclinic.com/Remedies/hydrogen_peroxide_inhalation.html-accessed on Jan. 29, 2010.*
Mr. Bill Munro's online statement concerning his inhalation of a 3% over-the-counter hydrogen peroxide composition readily available at drugstores: www.landrights.com/Hydrogen_Peroxide.htm-accessed on Jan. 29, 2010.*
A screenshot of an online vide of Mr. Bill Munro instructing the public on how he prepares an inhaler containing a hydrogen peroxide composition and administers the composition to himself daily: www.youtube.com/watch?v=aT1_Rkl0B1M—accessed on Jan. 29, 2010.*
Slungaard, A. et al., J. Biol. Chem., 1991 266:490-49103.
Banner, K.H. et al., Pumonary Pharmacol. 1995 8:37-42.
Salathe, et al. (1997) "Isolation and characterization . . . " Am. J. Respir. Cell Mol. Biol. 17:97-105.
Wang, et al. (1996) "NADPH-oxidase and a hydrogen . . . " Proc. Nat'l Acad. Sci. USA 93:13182-13187.
Bjorck, et al. (1975) "Antibacterial activity of the . . . " Applied Microbiol. 30:199-204.
Dacre and Tabershaw (1970) "Thiocyanate in Saliva and Sputum: Relationship to Smoking and Industrial Hygiene" Arch. Environmental Health 21:47-49.
Conner, et al. (2001) "Impaired thiocyanate transport . . . " Am. J. Respir. Critic. Care Med. 163:A490.
Lovaas (1992) "Free Radical Generation . . . " Free Radical Biol. and Med. 13:187-195.
Thomas, et al. (1994) "Antibacterial activity of hydrogen peroxide . . . " Infection and Immunity 62:529-535.

* cited by examiner

*Primary Examiner*—Johann R Richter
*Assistant Examiner*—James H Alstrum Acevedo
(74) *Attorney, Agent, or Firm*—John Storella

(57) ABSTRACT

Methods and devices useful for treatment of lung conditions resulting from dysfunction of normal pulmonary physiology.

24 Claims, No Drawings

METHODS AND DEVICES FOR TREATING LUNG DYSFUNCTION

CROSS-REFERENCES TO RELATED APPLICATIONS

This application claims benefit of U.S. Provisional Application No. 60/291,210, filed May 15, 2001, and is a continuation of U.S. Ser. No. 10/146,405, filed May 14, 2002 now U.S. Pat. No. 6,702,998, each of which is incorporated herein by reference.

FIELD OF THE INVENTION

The invention relates to methods and devices for treating various medical conditions, e.g., lung dysfunction. Some of the conditions are related to cystic fibrosis, and others may be more widely applicable.

BACKGROUND OF THE INVENTION

Cystic fibrosis (CF) is the most common life-shortening genetic disease in the white population. It occurs in the USA in about 1/3,300 white births, 1/15,300 black births, and 1/32,000 Asian-American births; 30% of patients are adults. See, e.g., Berkow (ed.) *The Merck Manual of Diagnosis and Therapy* Merck & Co., Rahway, N.J.; Thorn, et al. *Harrison's Principles of Internal Medicine* McGraw-Hill, N.Y.; and Weatherall, et al. (eds.) *Oxford Textbook of Medicine* Oxford University Press, Oxford; the Cystic Fibrosis Foundation website (www.cff.org); Davis (ed. 1993) *Cystic Fibrosis* Marcel Dekker, ISBN: 082478815X; Dodge (ed. 1996) *Cystic Fibrosis: Current Topics* Wiley & Son, ISBN: 0471963534; Bauernfeind, et al. (eds. 1996) *Cystic Fibrosis Pulmonary Infections: Lessons from Around the World* (Respiratory Pharmacology and Pharmacotherapy) Springer Verlag, ISBN: 081765027X; Orenstein and Stern (eds. 1998) *Treatment of the Hospitalized Cystic Fibrosis Patient* Marcel Dekker, ISBN: 0824795008; Hodson, et al. (eds. 2000) *Cystic Fibrosis* Oxford Univ. Press, ISBN: 0340742089; and Yankaskas and Knowles (eds. 1999) *Cystic Fibrosis in Adults* Lippincott Pubs, ISBN: 0781710111. See also Conese and Assael (2001) "Bacterial infections and inflammation in the lungs of cystic fibrosis patients" *Ped. Infect. Dis. J.* 20:207-213; Moss (2001) "New approaches to cystic fibrosis" *Hosp. Pract.* (Off. Ed.) 36:25-27, 31-32, 35-37; Robinson (2001) "Cystic fibrosis" *Thorax* 56:237-241; Ratjen (2001) "Changes in strategies for optimal antibacterial therapy in cystic fibrosis" *Int. J. Antimicrob. Agents* 17:93-96; Hodson (2000) "Treatment of cystic fibrosis in the adult" *Respiration* 67:595-607; Doring, et al. (2000) "Antibiotic therapy against *Pseudomonas aeruginosa* in cystic fibrosis: a European consensus" *Eur. Respir. J.* 16:749-767; Beringer and Appleman (2000) "Unusual respiratory bacterial flora in cystic fibrosis: microbiologic and clinical features" *Curr. Opin. Pulm. Med.* 6:545-550; Larson and Cohen (2000) "Cystic fibrosis revisited" *Mol. Genet. Metab.* 71:470-477; Nasr (2000) "Cystic fibrosis in adolescents and young adults" *Adolesc. Med.* 11:589-603; Rahman and MacNee (2000) "Oxidative stress and regulation of glutathione in lung inflammation" *Eur. Respir. J.* 16:534-554; and Koch and Hoiby (2000) "Diagnosis and treatment of cystic fibrosis" *Respiration* 67:239-247.

CF is typically carried as an autosomal recessive trait by about 3% of the white population. The most common gene responsible has been localized to 250,000 base pairs of genomic DNA on chromosome 7q (the long arm). This encodes a membrane-associated protein called the cystic fibrosis transmembrane regulator (CFTR). The most common gene mutation, F508, leads to absence of a phenylalanine residue at position 508 on the CFTR protein and is found on about 70% of CF alleles; >600 less common mutations account for the remaining 30%. Although the exact function of CFTR is unknown, it appears to be part of a cAMP-regulated $Cl^-$ channel and appears to regulate $Cl^-$ and $Na^+$ transport across epithelial membranes. Heterozygotes may show subtle abnormalities of epithelial transport but are clinically unaffected.

Fifty percent of affected patients present with pulmonary manifestations, usually chronic cough and wheezing associated with recurrent or chronic pulmonary infections. Cough is typically the most troublesome complaint, often accompanied by sputum, gagging, vomiting, and disturbed sleep. Intercostal retractions, use of accessory muscles of respiration, a barrel-chest deformity, digital clubbing, and cyanosis occur with disease progression. Upper respiratory tract involvement includes nasal polyposis and chronic or recurrent sinusitis. Adolescents may have retarded growth, delayed onset of puberty, and a declining tolerance for exercise. Pulmonary complications in adolescents and adults include pneumothorax, hemoptysis, and right heart failure secondary to pulmonary hypertension.

Cystic fibrosis still presents major health problems to afflicted individuals. It is a highly debilitating condition, and affects significant numbers of patients. As such, there is great need for new and more effective treatments. The present invention addresses these and other problems.

SUMMARY OF THE INVENTION

The present invention provides methods of treating a respiratory tract infection in a primate suffering from cystic fibrosis or other respiratory tract condition, comprising administering to the primate an effective amount of aerosolized thiocyanate or halides. In certain embodiments, the treating is after symptoms of bacterial infection have been detected or perhaps for viral infections instead or for bacterial infections that follow viral infections of the respiratory tract. Typically, the lung infection is: *Staphylococus aureus; Pseudomonas aeruginosa*; or *Burkholderia cepacia*. The method may be used in combination, e.g., with a peroxidase; $H_2O_2$; and/or another treatment for a lung infection or cystic fibrosis. Such other treatments may be, e.g., an antibiotic; an antiviral; an enzyme; or a manipulation, such as massage or percussive therapy, including breathing exercises, postural drainage, chest percussion, vibration, or assisted coughing.

In another embodiment, the invention provides methods of treating a respiratory infection, e.g., lung, in a mammal, comprising administering to the mammal an effective amount of thiocyanate or other halides, e.g., $I^-$, $Br^-$, etc. Often, the administering is: by aerosol inhalation of the thiocyanate; or in combination with: an antibiotic; an antiviral; an enzyme; $H_2O_2$; or a medical manipulation. The lung infection is likely to be: *Staphylococcus aureus; Pseudomonas aeruginosa*; or *Burkholderia cepacia*. In various embodiments, the effective amount of thiocyanate is between about 5 μM and 4 mM in the lung fluid; or the administering occurs between one administration in a week to hourly.

Another embodiment includes methods of treating a lung condition in a primate or rodent suffering from or exhibiting symptoms of cystic fibrosis, the method comprising administering to the lung of the creature an effective amount of thiocyanate. Typically, the administering is by inhalation of aerosolized thiocyanate; the creature is a mouse or rat; the creature suffers from a lung infection; or the treating further includes administration of a peroxidase or $H_2O_2$.

Another embodiment includes methods of treating a lung condition in a primate exhibiting symptoms of cystic fibrosis, comprising administering to the respiratory system of the primate an effective amount of $H_2O_2$. Typically, the administering is by inhalation of $H_2O_2$, or a formulation which produces $H_2O_2$ in the respiratory system; or the lung condition comprises infection with a bacterium, e.g., *Staphylococcus aureus*, *Pseudomonas aeruginosa*, or *Burkholderia cepacia*, fungus, or virus. Often, the administering is in combination with administering a peroxidase, thiocyanate, or another treatment for a lung condition, e.g., a lung infection or cystic fibrosis, such as administering an antibiotic, anti-fungal, anti-viral, enzyme, e.g., a depolymerase, or applying an airway clearance technique or physical therapy, e.g., breathing exercises, postural drainage, chest percussion, vibration, or assisted coughing. The $H_2O_2$ is often administered at a concentration between $10^{-7}$ M and $10^{-4}$ M in the lung fluid; or between once in a week to hourly.

Another embodiment includes methods of treating a lung infection in a mammal, the method comprising administering to the respiratory system of the mammal an effective amount of $H_2O_2$. Typically, the administering is by inhalation of $H_2O_2$; or a formulation is administered which produces $H_2O_2$ in the respiratory system; or the treatment prevents a minor or minimal lung infection from becoming more serious. Often the lung infection comprises a bacterium, e.g., *Staphylococcus aureus*, *Pseudomonas aeruginosa*, or *Burkholderia cepacia*, fungus, or virus; or the administering is in combination with peroxidase, thiocyanate, or an additional treatment for a lung condition, including a lung infection or cystic fibrosis. The additional treatment will often include an antibiotic, anti-fungal, anti-viral, enzyme, e.g., a depolymerase, or an airway clearance technique or physical therapy, e.g., breathing exercises, postural drainage, chest percussion, vibration, or assisted coughing. Typically the method will provide $H_2O_2$ at a concentration between $10^{-7}$ M and $10^{-4}$ M in the lung fluid; or between once in a week to hourly.

Yet another embodiment encompasses an inhaler comprising: hydrogen peroxide, a peroxidase, or thiocyanate. The inhaler may be labeled, e.g., include instructions, for administration to an individual with cystic fibrosis or other lung infection or condition. The inhaler may further comprise an antibiotic, antifungal, or antiviral therapeutic. The individual may have a lung infection or other symptoms of cystic fibrosis.

DETAILED DESCRIPTION OF THE INVENTION

Outline

I. Cystic Fibrosis
II. Current CF Treatments
III. The Lactoperoxidase (LPO) System
IV. Therapeutic Applications In accordance with the objects outlined above, the present invention provides novel methods for treating or preventing signs or symptoms of respiratory dysfunction, particularly infections resulting from compromised airway functions related to resistance to infectious agents which enter the body through the airway mucosa. Devices are provided which are useful in addressing these problems.

Descriptions of lung immunity is applicable to other parts of the respiratory tract. Since the mechanisms described herein are common to airways in general, the applications described would also apply to other airway mucosal surfaces.

I. Cystic Fibrosis

Cystic fibrosis is the most common genetic disorder among Caucasians. The disease is characterized by chronic respiratory infection that begins early in life with *Staphylococcus aureus* and *Haemophilus influenzae* infections and later colonization with mucoid strains of *Pseudomonas aeruginosa*. Chronic respiratory infection results in progressive loss of lung function and greatly diminished quality of life or shortened life expectancy. See references listed in the Background section. Chronic infection implies failure of airway host defense against bacterial colonization although the exact defects in host defense remain unclear. The normal airway barrier to infection is complex and multifactorial. The currently accepted view is that cilia mechanically clear potential infectious particles and that mucus provides both a protective barrier and serves as a carrier with the proper viscoelastic properties to permit ciliary movement. The protective barrier of mucus is thought to be both physical and chemical as a number of anti-microbial components are secreted by airway epithelial and submucosal gland cells. Lung physiology and function are fundamental clinical study areas, and are described, e.g., in Murray and Nadel (2001) *Textbook of Respiratory Medicine* Saunders, Philadelphia, Pa. (ISBN: 0721692532); Crystal, et al. (1996) *The Lung* Lippincott Williams & Wilkins, Philadelphia, Pa. (ISBN 0-397-51632-0); Brewis, et al. (1995) *Respiratory Medicine* 2d Ed., Saunders, Philadelphia, Pa. (ISBN: 0702016411); and Fraser, et al. (1988) *Diagnosis of Diseases of the Chest Volume* 3d Ed., Saunders, Philadelphia, Pa. (ISBN: 0721638708).

Additionally, nearly all exocrine glands are affected in varying distribution and degree of severity. Involved glands are of 3 main types: those that become obstructed by viscid or solid eosinophilic material in the lumen (e.g., pancreas, intestinal glands, intrahepatic bile ducts, gallbladder, submaxillary glands); those that are histologically abnormal and produce an excess of secretions (e.g., tracheobronchial and Brunner's glands); and those that are histologically normal but secrete excessive $Na^+$ and $Cl^-$ (e.g., sweat, parotid, and small salivary glands). Duodenal secretions are viscid and contain an abnormal mucopolysaccharide. The reproductive functions for both adult males and females are typically also affected.

Morbidity in cystic fibrosis (CF) primarily results from chronic respiratory infections by *Pseudomonas aeruginosa*. Mutations in CFTR result in an anion channel defect but how this leads to impaired host defense against infection is not fully understood. Evidence suggests that the lungs are histologically normal at birth. Pulmonary damage is probably initiated by diffuse obstruction in the small airways by abnormally thick mucus secretions. Bronchiolitis and mucopurulent plugging of the airways occur secondary to obstruction and infection. Bronchial changes are more common than parenchymal changes. Emphysema is not prominent. As the pulmonary process progresses, bronchial walls thicken; the airways fill with purulent, viscid secretions; areas of atelectasis develop; and hilar lymph nodes enlarge. Chronic hypoxemia results in muscular hypertrophy of the pulmonary arteries, pulmonary hypertension, and right ventricular hypertrophy. Much of the pulmonary damage may be caused by immune-mediated inflammation secondary to the release of proteases by neutrophils in the airways. Bronchoalveolar lavage fluid, even early in life, contains large numbers of neutrophils and increased concentrations of free neutrophil elastase, DNA, and interleukin-8.

Early in the course, *Staphylococcus aureus* is the pathogen most often isolated from the respiratory tract, but as the disease progresses, *Pseudomonas aeruginosa* is most frequently isolated. A mucoid variant of Pseudomonas is uniquely associated with CF. Colonization with *Burkholderia cepacia* occurs in up to 7% of adult patients and may be associated with rapid pulmonary deterioration.

II. Current CF Treatments

Many of the signs and symptoms of CF are pulmonary. Thus, chest x-ray findings often aid diagnosis. Hyperinflation and bronchial wall thickening are typically the earliest findings. Subsequent changes include areas of infiltrate, atelectasis, and hilar adenopathy. With advanced disease, segmental or lobar atelectasis, cyst formation, bronchiectasis, and pulmonary artery and right ventricular enlargement occur. Branching, fingerlike opacifications that represent mucoid impaction of dilated bronchi are characteristic. In almost all cases, sinus x-rays and CT studies show persistent opacification of the paranasal sinuses.

Pulmonary function tests typically reveal hypoxemia and reduction in forced vital capacity (FVC), forced expiratory volume in 1 sec (FEV1), and FEV1/FVC ratio and an increase in residual volume and the ratio of residual volume to total lung capacity. Fifty percent of patients have evidence of airway hyperreactivity.

Current treatment for pulmonary manifestations includes prevention of airway obstruction and prophylaxis against and control of pulmonary infection. Prophylaxis against pulmonary infections consists of maintenance of pertussis, and immunity to *Haemophilus influenzae*, varicella, measles, and influenza by vaccination. In unvaccinated patients, amantadine can be used for prophylaxis against influenza A.

Chest physical therapy consisting of postural drainage, percussion, vibration, and assisted coughing is recommended at the first indication of pulmonary involvement. In older patients, alternative airway clearance techniques such as active cycle of breathing, autogenic drainage, flutter valve device, positive expiratory pressure mask, and mechanical vest therapy may be effective. For reversible airway obstruction, bronchodilators may be given orally and/or by aerosol and corticosteroids by aerosol. $O_2$ therapy is indicated for patients with severe pulmonary insufficiency and hypoxemia. Noninvasive positive pressure ventilation by nasal or facemask also can be beneficial. Long-term daily aerosol administration of dornase alfa (recombinant human deoxyribonuclease) has been shown to slow the rate of decline in pulmonary function and to decrease the frequency of severe respiratory tract exacerbations. Other aspects of current treatment are known. See, e.g., *The Merck Manual*, and CF references listed above.

Drug therapies include oral corticosteroids for infants with prolonged bronchiolitis and in those patients with refractory bronchospasm, allergic bronchopulmonary aspergillosis, and inflammatory complications (e.g., arthritis and vasculitis). Long-term use of alternate-day corticosteroid therapy can slow the decline in pulmonary function, but because of steroid-related complications it is not recommended for routine use. Patients receiving corticosteroids must be closely monitored for evidence of carbohydrate abnormalities and linear growth retardation. Ibuprofen, when given at a dose sufficient to achieve a peak plasma concentration between 50 and 100 µg/ml over several years, has been shown to slow the rate of decline in pulmonary function, especially in children 5 to 13 yr. The appropriate dose must be individualized based on pharmacokinetic studies.

Antibiotics should be used in symptomatic patients to treat bacterial pathogens in the respiratory tract, according to culture and sensitivity testing. A penicillinase-resistant penicillin (e.g., cloxacillin or dicloxacillin) or a cephalosporin (e.g., cephalexin) is the drug of choice for staphylococci. Erythromycin, amoxicillin-clavulanate, ampicillin, tetracycline, trimethoprim-sulfamethoxazole, or occasionally chloramphenicol may be used individually or in combination for protracted ambulatory therapy of pulmonary infection due to a variety of organisms. Ciprofloxacin is effective against sensitive strains of *Pseudomonas*. For severe pulmonary exacerbations, especially in patients colonized with *Pseudomonas*, parenteral antibiotic therapy is advised, often requiring hospital admission but safely conducted at home in carefully selected patients. Combinations of an aminoglycoside (tobramycin, gentamicin) with an anti-*Pseudomonas* penicillin are given IV. Intravenous administration of cephalosporins and monobactams with anti-*Pseudomonas* activity also may be useful. Serum aminoglycoside concentrations should be monitored and dosage adjusted to achieve a peak level of 8 to 10 µg/ml (11 to 17 µmol/L) and a trough value of <2 µg/ml (<4 µmol/L). The usual starting dose of tobramycin or gentamicin is 7.5 to 10 mg/kg/day in 3 divided doses, but high doses (10 to 12 mg/kg/day) may be required to achieve acceptable serum concentrations. Because of enhanced renal clearance, large doses of some penicillins may be required to achieve adequate serum levels. The goal of treating pulmonary infections should be to improve the clinical status sufficiently so that continuous use of antibiotics is unnecessary. However, in some ambulatory patients with frequent pulmonary exacerbations, long-term use of antibiotics may be indicated. In selected patients, long-term tobramycin therapy by aerosol may be effective.

Aerosol therapy with ribavirin should be considered in infants with respiratory syncytial viral infection. Levels of airway glutathione have been shown to be reduced in the airway lavages and in plasma of cystic fibrosis patients. In vitro studies of airway lining cells from normal and cystic fibrosis patients have shown that cystic fibrosis cells are defective in glutathione transport compared to normal and that replacement of the defective gene product restores glutathione transport. Since the LPO system can oxidize glutathione and since microorganisms have specific uptake systems for glutathione, and since glutathione is deficient in cystic fibrosis, combination therapies with all or part of the LPO system and glutathione may provide increased efficacy or may be necessary for system function.

That lung infections are problematic in CF is evidenced by the recent activity in this area. The first new drug therapy developed exclusively for CF in 30 years was approved by the Food and Drug Administration (FDA) in 1993. In clinical trials, this mucus-thinning drug called Pulmozyme®, reduced the number of respiratory infections and improved lung function. In 1995, a four-year CF Foundation-supported study showed that the drug, ibuprofen, reduced the rate of lung inflammation in children with CF—under controlled conditions, and in high doses. This is a DNAse that liquifies secretions that are containing large amounts of bacterial DNA.

In late 1997, the FDA approved the drug TOBI™ (tobramycin solution for inhalation). In clinical trials, this reformulated version of the common antibiotic improved lung function in people with CF and reduced the number of hospital stays. The benefits of TOBI™ are that it can be delivered in a more concentrated dose directly to the site of CF lung infections more efficiently, and that it is preservative-free. The development of TOBI™ should lead to a long line of other aerosolized antibiotics for people with CF.

Beyond currently available antibiotics, the CF Foundation pursues novel strategies that will lead to entirely new forms of antibiotics, i.e., to clear lung infections. The promising compound, IB367, represents one of an up-and-coming new class of drugs that should provide physicians unique tools to better manage chronic CF lung infections.

In CF cells, salt does not move properly because the protein product of the CF gene is defective—and makes a faulty channel for the salt (chloride) to exit. Scientists are therefore looking for ways to get the chloride out of cells. INS365 is being evaluated for its ability to stimulate cells to secrete chloride. This, in turn, should lead to mucus that is less thick and sticky.

Other therapeutics in development are described in the Cystic Fibrosis Foundation website. Among Phase III clinical trial candidates are protein-assist and chloride channel strategy therapeutics and anti-inflammatory and anti-infection therapeutics.

The protein-assist and chloride channel strategies attempt to correct the defective CFTR protein or at least get enough protein to the cell surface, where it can operate as a channel. For people who do not have CF, the CFTR protein acts as a "one-way door" that allows cells to release chloride. However, for people with CF, this protein is defective, which leads to improper chloride balance and the thick, sticky CF mucus. Chloride channel therapies are another exciting method of correcting the defect in CF cells. Researchers believe that getting CF cells to release chloride would be of a tremendous therapeutic benefit for CF patients.

Anti-inflammatory and anti-infection therapies are directed to medications that help control infection and inflammation because these CF symptoms tear down airways in a dangerous cycle. When CF lungs become infected, they also become over-inflamed. This over-inflammation leads to a greater susceptibility to future infection. Breaking or preventing this destructive cycle is a key focus for CF research. Although these therapies do not target the basic defect in CF cells, there are many exciting medications being evaluated that could extend lives by stemming the course of dangerous infections and the resulting accumulation of damage.

The present invention provides another therapeutic. While not limited according to mechanism, the present invention would seem to be based, in part, upon insight into the natural systems of lung immunity which appear to be compromised in CF.

III. The Lactoperoxidase (LPO) System

The lactoperoxidase (LPO) antibiotic system, shown to participate in ovine airway host defense, requires the anion thiocyanate ($SCN^-$) in airway secretions for its function. To test the hypothesis that CF mutations lower airway [$SCN^-$] thereby leading to impaired LPO-mediated host defense, human airways were examined for an LPO system. Normal and CF epithelial cell cultures were compared for differences in $SCN^-$ transport that could be functionally linked to CF. LPO and $SCN^-$ were found in human airway secretions and LPO mRNA was found in trachea tissue. In air liquid interface cultures, normal human airway epithelia transported $SCN^-$ from the basolateral to the apical compartment and concentrated the anion at the mucosal surface with pharmacological properties consistent with CFTR-mediated channel activity. The pharmacological characteristics of $SCN^-$ transport implied at least an indirect role of CFTR. $SCN^-$ transport and apical $SCN^-$ accumulation were significantly reduced in CF cultures. This alteration in $SCN^-$ transport suggests a simple mechanistic link between CF mutations and the LPO host defense system in human airway.

The cystic fibrosis gene product, cystic fibrosis transmembrane regulator (CFTR), contains an anion channel that has been extensively characterized and mutations result in loss of functional CFTR anion channel activity on the apical cell surface. The current controversy regarding the link between cystic fibrosis and defective airway host defense has been reviewed by others and centers on the exact determination of the ionic composition of airway surface liquid (ASL) and the volume of ASL in cystic fibrosis versus normal airways. Opposing views focus on either the effects of dehydration and impaired ciliary clearance of mucus or the effects of hypertonic ASL on the activity of antimicrobials in mucus. Both views are limited by our incomplete knowledge regarding the total array of mechanisms at work in airway host defense.

For example, the lactoperoxidase (LPO) system has recently been shown to be important to clear bacteria from sheep airways (Gerson, et al. (2000) *Am. J. Respir. Cell Mol. Biol.* 22:665-671) although its existence in human airways has not previously been shown. The LPO antibiotic system works to preserve milk sterility and contributes antibiotic activity to saliva. LPO uses $H_2O_2$ to catalyze oxidation of the anions $SCN^-$ (a pseudohalide) and some halides (e.g., $I^-$ and $Br^-$) to the antibiotic forms (e.g., $OSCN^-$, $OI^-$, or $OBr^-$). Thomas, et al. (1991), pp. 123-142, in Everse, et al (eds.) *Peroxidases in Chemistry and Biology*. Descriptions will be directed to $SCN^-$, but similarly, $I^-$ and $Br^-$ may be substituted.

$$H_2O_2 + SCN^- \xrightarrow{LPO} OSCN^- + H_2O$$

Since it is known that the LPO system is effective against pseudomonads (Bjorck, et al. (1975) *Applied Microbiology* 30:199-204), and that $SCN^-$ is a requisite substrate for LPO and is permeant through CFTR (Tabcharani, et al. (1993) *Nature* 366:79-82), defects in $SCN^-$ transport could be, at least partially, responsible for the chronic respiratory bacterial infections seen in CF patients. Described experiments herein support the hypothesis that the LPO system is present in human airways and that cystic fibrosis airway epithelia are defective in $SCN^-$ transport to the airway surface.

The experiments presented here document the presence of the lactoperoxidase anti-microbial system in human airways that was not previously recognized as a factor in human airway host defense. The data also show that the secretion of LPO's substrate, $SCN^-$, appears to rely, at least indirectly, on the CFTR anion channel and that mutant CFTR results in defective delivery of LPO's substrate to the airway lumen.

*Pseudomonas* infection occurs with high frequency in CF airways and the LPO system's efficacy against pseudomonads has been previously documented. Bjorck, et al. (1975) *Applied Microbiology* 30:199-204. Defective $SCN^-$ transport in CF may impair the correct functioning of the LPO antibiotic system and be a contributor to the characteristic chronic respiratory infections seen in this disease. $SCN^-$ is elevated in CF sweat (Gibbs and Hutchings (1961) *Proc. Soc. Exp. Biol. Med.* 106:368-369) and others have suggested that $SCN^-$ might be a pathogenic factor in CF based on decreased serum levels in severely affected CF patients compared to normal individuals (which would predict an even lower concentration in CF airways than that calculated above). Weuffen, et al. (1991) *Padiatrie und Grenzgebiete* 30:205-210.

Several mouse models of cystic fibrosis have been developed and none show the characteristic chronic airway infection seen in the human disease. Murine respiratory tracts were examined for the presence of LPO or an LPO-like protein by collecting tracheal secretions and assaying enzyme activity. Attempts to demonstrate an LPO system in airways of normal mice failed, e.g., in mice whose airways were challenged with live bacteria, or in mice previously sensitized and challenged with ovalbumin in order to up-regulate secretory cells in the airways. Since LPO is made by airway submucosal glands and goblet cells (Gerson, et al. (2000) *Am. J. Respir. Cell Mol. Biol.* 22:665-671; and Salathe, et al. (1997) *Am. J. Respir. Cell Mol. Biol.* 17:97-105), the lack of these structures in mouse airways suggested that LPO may not be present in this animal's respiratory tract and that mice may rely on an alternate airway defense. Lack of reliance on an LPO system could explain, in part, why CFTR knockout mice do not display the chronic respiratory infection characteristic of cystic fibrosis.

One unexplained feature of chronic infection in CF is the inability of neutrophils to clear bacteria. CF airways are characterized by a constant high level of lumenal neutrophils that appear to be competent in phagocytosis, chemotaxis, and have functional myeloperoxidase (MPO). Yet bacterial infection is not resolved even in the presence of aggressive antibiotic therapies, suggesting a defect in neutrophil killing. Although mucoid strains of *Pseudomonas* are present in later stages of CF, defects in host defense and neutrophil mediated killing exist in earlier stages of the disease suggesting that mucoid character alone does not explain the inability of neutrophils to resolve infections. MPO uses $Br^-$, $I^-$, $Cl^-$, and $SCN^-$ as substrates and although most studies of MPO-mediated bacterial killing have concentrated on use of $Cl^-$, $SCN^-$ has recently been shown to be the preferred substrate of MPO. Thus impaired $SCN^-$ transport to the lumen could potentially result in defects in both the epithelial-derived LPO system as well as the neutrophil-derived MPO antibacterial activity. The $SCN^-$ deficiency may be doubly detrimental to maintenance of a sterile airway.

Because the LPO antimicrobial system relies on correct $SCN^-$ anion concentration rather than osmolarity of ASL or water volume, measures of these ASL characteristics are not expected to be relevant to LPO antibacterial activity. The total loss of airway lumenal $SCN^-$ would probably not be detected in measurement of ASL ionic strength or tonicity as it is $\leq 1$ mM in ASL of normal airways. Elemental analysis of ASL has demonstrated large amounts of sulfur that have been ascribed to the presence of sulfated mucins and that may obscure the detection of $SCN^-$ in these studies.

Taken together with the extensive literature on mutant CFTR-linked changes in the airway, the data presented here suggest that defective $SCN^-$ transport to the airway may account for a portion of the chronic infection seen in cystic fibrosis and that aerosol $SCN^-$ therapy may bolster airway host defense against infection in patients with this disease.

Since the LPO system has been shown to be functional in the ovine airways and in secretions collected from human airways (Wijkstrom-Frei, et al. (2003) *Am. J. Respir. Cell and Mol. Biol.* 29:206-212), not only $SCN^-$, but also $H_2O_2$ concentration in the airway surface liquid is important in full expression of LPO system activity.

IV. Therapeutic Application

According to the present invention, methods for treating various respiratory system conditions are provided, particularly those related to respiratory system response to infectious agents. These conditions are typical of the normal or dysfunctional respiratory tract in a mammal, e.g., primate, sheep, rodent, or common domestic pet, including dogs and cats. The present disclosure provides evidence for a natural response to airway infections in primates. This system, the LPO system, is implicated as a mechanism to decrease likelihood of established colonization of microbes in the lung.

These reagents can be combined for therapeutic use with additional active or inert ingredients, e.g., in conventional pharmaceutically acceptable carriers or diluents, e.g., immunogenic adjuvants, along with physiologically innocuous stabilizers, excipients, or preservatives. These combinations can be sterile filtered and placed into dosage forms as by lyophilization in dosage vials or storage in stabilized aqueous preparations.

The LPO system is found in the lung of at least some species. In those species, including certain primates, the presence of that system should provide antibacterial function, which should be generally effective against most common infectious bacterial and fungal species. The enzymatic conversion of the anion SCN— to the antimicrobial OSCN— results in a means to decrease microbial load to the lung. Other species, which lack the LPO system, may serve as species useful for testing whether the introduction of such a system may be of value in certain lung infection models.

Since the lung fluid, which bathes the mucosa, is the target of treatment, an aerosol is the preferred method of administration. While other means to administer to the lung will be available, there is a great deal of inhaler art. Here, with the administration of small molecules, or perhaps in combination with a biologic, the inhalers are preferred means for administration. See, e.g., U.S. Pat. No. 6,223,746 "Metered dose inhaler pump"; U.S. Pat. No. 6,205,999 "Methods and apparatus for storing chemical compounds in a portable inhaler"; U.S. Pat. No. 6,204,054 "Transcytosis vehicles and enhancers for drug delivery"; U.S. Pat. No. 6,202,643 "Collapsible, disposable MDI spacer and method"; U.S. Pat. No. 6,196,219 "Liquid droplet spray device for an inhaler suitable for respiratory therapies"; U.S. Pat. No. 6,196,218 "Piezo inhaler"; U.S. Pat. No. 6,182,655 "Inhaler for multiple dosed administration of a pharmacological dry powder"; U.S. Pat. No. 6,180,663 "Therapeutic nasal inhalant"; U.S. Pat. No. 6,176, 238 "Dispenser for substances in powder or granular form"; U.S. Pat. No. 6,170,482 "Inhalation apparatus"; U.S. Pat. No. 6,165,484 "EDTA and other chelators with or without antifungal antimicrobial agents for the prevention and treatment of fungal infections"; U.S. Pat. No. 6,164,275 "Inhaler carrier"; U.S. Pat. No. 6,158,428 "Infant inhaler"; U.S. Pat. No. 6,155,251 "Breath coordinated inhaler"; U.S. Pat. No. 6,153, 224 "Carrier particles for use in dry powder inhalers"; U.S. Pat. No. 6,153,173 "Propellant mixture for aerosol formulation"; U.S. Pat. No. 6,149,892 "Metered dose inhaler for beclomethasone dipropionate"; U.S. Pat. No. 6,142,146 "Inhalation device"; U.S. Pat. No. 6,142,145 "Inhalation device"; U.S. Pat. No. 6,140,323 "Dosing method of administering medicaments via inhalation administration or skin administration"; and U.S. Pat. No. 6,138,673 "Inhalation device and method". Many others may be found by a simple search through a patent database.

As such, the treatment described herein is intended to decrease the microbial load in an infected lung by a significant and measurable amount or to reduce the frequency of infection establishment in a normal lung exposed to infectious agents. While the normal lung may possess sufficient LPO to convert inhaled thiocyanate to an activated antimicrobial product, certain lung conditions may deplete the thiocyanate, $H_2O_2$ or LPO, whose supplementation may overcome dysfunction resulting therefrom. Thus, the treatment is intended to decrease the microbial flora in an infected airway by at least about 10%, preferably at least about 20%, more preferably by at least about 50%, and better by at least 2, 3, 5, or 7 fold. Other relevant endpoints would be sputum neutrophil counts, sputum volume production, pulmonary function testing, incidence of hospitalization among a population of patients, or chest X-ray evaluation, which would improve by similar measures, e.g. 10%, 20%, 50%, or multifold, according to treatment. Such measures will be taken at appropriate time points, as clinically significant. Such may be at specified time points after microbial exposure or introduction, and may range from minutes, hours, days, or weeks after defined identifiable events.

Treatment dosages should be initially titrated in development to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) *Goodman and Gilman's: The Pharmacological Bases of Therapeutics*, latest Ed., Pergamon Press; and *Remington's Pharmaceutical Sciences*, latest ed., Mack Publishing Co., Easton, Pa. Methods for administration are discussed therein and below, e.g., for direct application to the lung. Pharmaceutically acceptable carriers will include water, saline, buffers, and other compounds described, e.g., in the *Merck Index*, Merck & Co., Rahway, N.J. Dosage ranges for $SCN^-$ would ordinarily be expected to deliver amounts that result in mucosal surface liquid concentrations lower than 10 mM concentrations, typically less than about 4 mM concentrations, preferably about 400 µM, preferably not less than about 4 µM. Slow release formulations, or a slow release apparatus may be utilized for continuous or long term administration. See, e.g., Langer (1990) *Science* 249:1527-1533. Dose evaluation may depend, e.g., on patient weight, age, condition, and other relevant variables. Exemplary dose ranges should account for total ASL and estimated sputum volumes. It is expected that normal amounts would be about 400 µM. The balance of excess activity versus tolerable damage from excess may depend on patient condition. Final concentrations would likely be in the 40 µM to 400 µM range.

Dosage amount for $H_2O_2$ would ordinarily be expected to deliver amounts that result in mucosal surface liquid concentrations lower than 100 µM concentrations, e.g. in concentrations which may be in the range of 0.1 to 1 or 10 µM.

Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for lung administration. The formulations may conveniently be presented in unit dosage form and may be prepared by many methods well known in the art of pharmacy. See, e.g., Gilman, et al. (eds. 1990) *Goodman and Gilman's: The Pharmacological Bases of Therapeutics* 8th Ed., Pergamon Press; and *Remington's Pharmaceutical Sciences,* 17th ed. (1990), Mack Publishing Co., Easton, Pa.; Avis, et al. (eds. 1993) *Pharmaceutical Dosage Forms: Parenteral Medications* Dekker, N.Y.; Lieberman, et al. (eds. 1990) *Pharmaceutical Dosage Forms: Tablets* Dekker, N.Y.; and Lieberman, et al. (eds. 1990) *Pharmaceutical Dosage Forms: Disperse Systems* Dekker, N.Y. The therapy of this invention may be combined with or used in association with other agents, e.g., other lactoperoxidase substrates or therapies.

As indicated above, various combinations of therapeutics may be used, e.g., with antibiotics, antifungal agents, antiviral agents, with various peroxidases, with sulfhydryl compounds, or other therapeutics or procedures used in the treatment of CF or other lung infections. Such procedures include airway clearance techniques (ACTs) and physiotherapy, e.g., breathing exercises, postural drainage, chest percussion, vibration, assisted coughing, and forced expiratory techniques. Other lung conditions will include those where infections may be problematic, e.g., tuberculosis, asthmatic conditions, artificially ventilated patients, HIV or other immunosuppressed individuals. As described above, there are various treatments for cystic fibrosis, which may be combined with the treatment described herein. Administration may be simultaneous or sequential, e.g., with the various other therapeutics, or with the DNAse (Pulmozyme®) or TOBI™.

Certain precautions would be indicated when administering thiocyanate and/or $H_2O_2$. To limit the possibility of thiocyanate toxicity, other sources of thiocyanate should be carefully monitored. Dietary sources include consumption of cauliflower, Brussels sprouts, and other cyanogenic compounds, e.g., various seeds from squashes such as pumpkin. Smoking, exposure to welding fumes, or diesel exhaust should be controlled. The monitoring of blood thiocyanate levels may be useful, including determination of swallowed and absorbed compound. Serum and urine thiocyanate should be measured at appropriate times, e.g., 1, 4, 8 h following initial administration, and perhaps during treatment. Clinical parameters may also be monitored, e.g., body temperature, volume or rate of respiration, various subjective measures of lung infection or cystic fibrosis symptoms.

Side effects of treatment may include expected fever from bacterial lysis. Excessive levels of $SCN^-$ may itself lead to toxic effects on the host.

Indications for use of the invention will include other respiratory tract conditions, e.g., beyond CF. Because of the ease of administration and low cost of the materials in the treatment described, the supplementation of the endogenous barrier to lung infections may be useful in many contexts. The circumstances in which lung infections may be problematic are well known in the art. See, e.g., Crystal, et al. (1996) *The Lung* Lippincott, ISBN 0-397-51632-0; and other lung references.

Thus, the present invention may become adopted as standard means to treat generic respiratory tract infections as a first and immediate step.

EXAMPLES

Example I

General Methods

Collection of Secretions and Tissues

Airway secretions were obtained from intubated patients undergoing ambulatory outpatient elective surgery according to IRB approved protocols. Patients were selected for not having respiratory disease. Saline (3 ml) was injected into the tracheal tube and immediately suctioned into a trap. Recovered secretions were spun at 16000 rpm for 20 min. at 4° C. The supernatant was aliquoted and stored at −80° C. for later analysis.

Western Blotting

Anti-LPO antiserum was prepared by immunizing rabbits with chromatographically purified sheep airway LPO (Gerson, et al. (2000) *Am. J. Respir. Cell Mol. Biol.* 22:665-671) that was further enriched by excision and elution from SDS gels. Affinity purification of LPO specific antibodies was performed using bovine milk LPO (Sigma Chemical) coupled to Sepharose. Control antibodies were IgGs prepared from un-immunized rabbits.

PCR

Human tracheal mRNA was purchased from Clontech (Palo Alto, Calif.). ds-cDNA was made using the SuperScript kit from Life Technologies (Bethesda, Md.) and size fractionated. Transformation into *E. coli* DH10α gave $5 \times 10^5$ independent colonies. Degenerate oligonucleotides were designed from conserved regions of mammalian heme peroxidases.

Cell Culture and Thiocyanate Transport Experiments

Airway epithelial cell cultures were grown and differentiated on either 6.5 mm or 24 mm collagen-coated T-clear membranes (Costar #3450) at an air-liquid interface. Bernacki, et al. (1999) *Am. J. Respir. Cell Mol. Biol.* 20:595-604. Experiments comparing non-CF and CF cells were performed with cultures grown simultaneously and matched in passage number, the number of cells plated, and days in culture. Cultures typically had a resistivity $\geq 300$ Ω·cm. Apical surfaces of cultures were washed with PBS and then incubated overnight with 70 µM $^{14}$C—SCN$^-$ (50 µCi/mM) in the basolateral media. To initiate experiments, apical surfaces of the cultures were rapidly washed three times with Dulbecco's PBS (50 µl for 6.5 mm filters or 500 µl for 24 mm filters) containing 100 µM amiloride. Following a third wash, additional aliquots were placed on the apical surface for sequential 2 min incubations at 37° C. in humidified 5% $CO_2$. PKA stimulation of SCN$^-$ efflux was demonstrated by adding 500 µM dibutryl cAMP and 10 µM forskolin to the PBS washes. The stimulated efflux was inhibited by further addition of 500 µM glibenclamide to washes containing dibutryl cAMP and forskolin. Basolateral media were sampled after the last wash and $^{14}$C—SCN$^-$ in media and apical washes was determined by liquid scintillation counting. The collected $^{14}$C—SCN$^-$ was soluble following 10% TCA precipitation showing that radiolabel was not covalently attached to protein.

Example II

LPO System in CF Patients

A hypothesis that the LPO system may be defective in cystic fibrosis was tested. Human airways were tested for the presence of an LPO antibiotic system. To assay for the presence of LPO in the airway lumen with negligible contamination by saliva (that also contains LPO), secretions were collected by suctioning intubated patients who were undergoing elective surgery and did not have active pulmonary disease. Assays of these secretions (Thomas, et al. (1994) *J. Dental Res.* 73:544-555; and Salathe, et al. (1997) *Am. J. Respir. Cell Mol. Biol.* 17:97-105) showed the presence of LPO activity and Western blot analysis of tracheal secretions demonstrated the presence of anti-LPO immuno-reactive bands, equivalent in $MW_{app}$ to that reported for human milk (Shin, et al. (2000) *J. Nutr. Biochem.* 11:94-102) and salivary (Mansson-Rahemtulla, et al. (1988) *Biochemistry* 27:233-239) LPO.

To demonstrate that the LPO detected by enzymatic assays was made in the airway, human tracheal mRNA was used to construct a cDNA library. Two degenerate oligonucleotides complementary to conserved regions of mammalian heme peroxidases were used to screen the library by PCR. This identified a partial cDNA (GenBank:AF027971) identical to human salivary (see GenBank:U39573) and milk LPO (see GenBank:M58151). These data demonstrated that human airways synthesized and secreted enzymatically active LPO into the airway lumen.

To function as an antibiotic system, LPO requires both SCN$^-$ and $H_2O_2$ as substrates. $H_2O_2$ has been identified in human airways previously. See Wang, et al. (1996) *Proc. Nat'l Acad. Sci. U.S.A* 93:13182-13187; Dohlman, et al. (1993) *Am. Rev. Respir. Dis.* 148:955-960; Antczak, et al. (1997) *Eur. Respir. J.* 10:1235-1241; and Jobsis, et al. (1997) *Eur. Respir. J.* 10:519-521. SCN$^-$ is found in salivary and gastric secretions but has not been conclusively demonstrated in human airways. Previously, reports of SCN$^-$ in human sputum (Dacre and Tabershaw (1970) *Arch. of Environ. Health* 21:47-49) were believed to represent saliva contamination because SCN$^-$ was below detection levels in airway secretions collected by bronchoscopic lavage. Since the large dilutions associated with bronchoalveolar lavage also resulted in false negative [SCN$^-$] in sheep, SCN$^-$ was measured in human tracheo-bronchial secretions collected without dilution from patients with no apparent lung disease intubated for reasons other than respiratory failure in the medical intensive care unit. SCN$^-$ assays (Densen, et al. (1967) *Arch. Environ. Health* 14:865-874) revealed the presence of detectable SCN$^-$. The concentration was within the ranges reported in saliva and gastric secretions, ruling out that the SCN$^-$ measured was due to minor amounts of saliva contamination. The measured [SCN$^-$] was high enough to serve as a substrate for LPO (Pruitt, et al. (1988) *Biochemistry* 27:240-245) and thus, together with the presence of LPO and $H_2O_2$, comprises an intact LPO antibiotic system in human airways.

Serum SCN$^-$ is thought to be derived primarily from diet either directly or by conversion from cyanide. Since mean normal non-smoking plasma SCN$^-$ values (40-50 µM; see Lundquist, et al. (1995) *Eur. J. Clin. Chem. Clin. Biochem.* 33:343-349) are substantially lower than the levels measured in airway secretions, the data suggest that SCN$^-$ is actively accumulated in airway secretions.

There are several possible approaches to determine if CF airway secretions might contain less SCN$^-$. Direct analysis of these fluids is complicated by high viscosity and infection. High viscosity makes accurate sample collection difficult and this may explain the conflicting reports (Boucher (1994) *Am. J. Respir. Crit. Care. Med.* 150:271-281) from previous analyses of ionic composition of CF secretions. Infection results in high concentrations of neutrophil-derived myeloperoxidase that also oxidizes SCN$^-$ (Thomas and Fishman (1986) *J. Biol. Chem.* 261:9694-9702). For these reasons, epithelial cell cultures were chosen for these experiments to test whether CF airway secretions might be deficient in their ability (or lack thereof) to transport SCN$^-$ from the serosal (basolateral) to the mucosal (apical) surface.

Example III

In vitro Evaluation of LPO System Relating to CF

Bronchial epithelial cells were obtained from either CF or non-CF lungs at the time of transplant or organ donation. Cells were passaged twice (thereby de-differentiated) and then cultured at an air-liquid interface for re-differentiation. See Bernacki, et al. (1999) *Am. J. Respir. Cell Mol. Biol.* 20:595-604. Between 1 and 3 weeks after exposure of the apical surface to air, the cultures were secreting mucus and cilia were present. To measure the flux of SCN$^-$ across the epithelium, $^{14}$C—SCN$^-$ (70 µM) was added to the basolateral media and 18-24 h later, its rate of efflux onto the apical surface liquid was monitored. Following three rapid PBS washes of the apical surface, additional PBS aliquots were placed on the apical surface for sequential 2 min incubations.

The appearance of $^{14}C$—$SCN^-$ in washes was used to measure efflux rates. Airway epithelial cell cultures from three separate CF patients were compared to three non-CF control cultures. In each case, CF cells showed significantly reduced (~4 fold) $SCN^-$ efflux rates.

Since CFTR mutants have alterations in anion channel activity, compounds known to stimulate or inhibit CFTR activity were used to evaluate a possible contribution of CFTR to the $SCN^-$ efflux in cultures. Non-CF cultures showed an increase in efflux after stimulation of PKA by dibutryl cAMP (0.5 mM) and forskolin (10 µM), while CF cultures did not. In non-CF cells, the PKA-stimulated and baseline $SCN^-$ efflux was blocked by glibenclamide (500 µM), but not by 4,4'-diisothiocyanostilbene-2,2'disulphonic acid (DIDS) or 4,4'-diinitrostilbene-2,2'disulphonic (DNDS). The glibenclamide inhibition was reversible. In CF cells, on the other hand, neither glibenclamide nor DIDS had any effect. Thus $SCN^-$ efflux in the cultures resembled the anion channel activity of CFTR with regard to response to these agents.

The differences in $SCN^-$ efflux between non-CF and CF cultures were independent of the age of the cultures (repeated measurements from 2-8 week old cultures), suggesting that a possible difference in time to reach full differentiation between CF and non-CF cells was not responsible for these observations. The fact that efflux was stimulated by cAMP and reversibly sensitive to glibenclamide argues strongly that the measured transepithelial $SCN^-$ flux was not due to leakage via a paracellular route. The same properties, along with the insensitivity to disulphonic stilbenes, suggest that, at the very least, the measured $SCN^-$ efflux is indirectly related to functional CFTR and perhaps even carried by CFTR itself. This notion is further supported by the fact that CF epithelial cells did not carry $SCN^-$ efficiently.

Exact determination of accumulated apical $[SCN^-]$ was not possible in these experiments because the naturally present small apical surface volumes in the air-liquid interface cultures normally prevented accurate sampling or even measurements by dilution. However comparison of the total amounts of $SCN^-$, recovered in the initial PBS wash of the apical surface after overnight incubations with $^{14}C$—$SCN^-$ in the basolateral media, showed 11-fold higher levels in non-CF compared to CF cultures. Although CF cultures are reported to have about one half the amount of apical surface fluid when compared to non-CF (Matsui, et al. (1998) *Cell* 95:1005-1015), the difference in accumulated apical $^{14}C$—$SCN^-$ between CF and non-CF cultures would remain significant (~5.5 fold) if this volume difference is taken into account. Thus, it appears that non-CF epithelial layers accumulate $SCN^-$ to significantly higher levels than CF. Interestingly, on the occasions that apical surface liquid was visible on non-CF cultures that had been pre-incubated with basolateral $^{14}C$—$SCN^-$, direct sampling (2-5 µl) allowed measurement of the $[SCN^-]$ and showed that it was concentrated ~6 fold over the 0.07 mM in the basolateral media to 0.4 mM. This concentration of $SCN^-$, measured in undiluted non-CF apical surface liquid, is similar to levels measured in undiluted airway secretions collected from patients. Liquid was never observed on the apical surface of CF cultures, as expected. Matsui, et al. (1998) *Cell* 95:1005-1015. Therefore, direct measurement of $[SCN^-]$ in CF apical surface fluid could not be made. However, by estimating the values for CF cells using the difference to non-CF cells measured above (~5.5 fold), the apical $SCN^-$ concentration appears likely to be close to that in the basolateral media.

Since these results suggested that $SCN^-$ was concentrated in the apical surface liquid over that in the basolateral media in normal cell cultures, the effect of increasing $[SCN^-]$ in the apical PBS washes was tested on $SCN^-$ efflux in these cells. Non-CF cultures transported $SCN^-$ into apical PBS washes containing 1-5 mM $SCN^-$, showing that the cells were able to concentrate $^{14}C$—$SCN^-$.

The measured/estimated difference in apical $[SCN^-]$ between CF and non-CF airway epithelial cells is expected to be functionally significant since previous studies on bovine milk LPO kinetic properties (Pruitt, et al. (1988) *Biochemistry* 27:240-245) show that a 5 fold decrease in the $[SCN^-]$ in this concentration range could potentially result in, a 100 fold decrease in LPO enzyme activity. Thus, the disparity in $SCN^-$ transport and apical concentration between CF and non-CF epithelia, reported here, would be expected to have a dramatic effect on the efficacy of this host defense mechanism. This implication could not be tested using collected apical surface liquid because these cultures did not synthesize and secrete reproducibly measurable LPO.

Example IV

LPO System Serves Antibacterial Function

Human airway secretions were obtained from intubated patients undergoing ambulatory outpatient elective surgery according to IRB approved protocols. Patients were selected for not having respiratory disease. Saline (3 ml) was injected into the tracheal tube and immediately suctioned into a trap. Recovered secretions were spun at 16,000 rpm for 20 min. at 4° C. The supernatant was aliquoted and stored at −80° C. for later analysis. Undiluted secretions were obtained from acutely (<24 h) intubated patients in the medical ICU who were intubated for reasons other than respiratory disease. Selected patients had no clinical signs of respiratory infection. Secretions were cleared by centrifugation (100,000×g, 30 min), aliquoted, and stored at −80° C.

Assay of Antibacterial Activity

*Pseudomonas aeruginosa* (ATCC 27853) were grown in LB broth overnight at 37° C. in a rotary shaker. Bacteria were collected in the stationary phase of growth and further diluted in LB broth to $5-6 \times 10^4$/ml. After adding glycerol to 15%, aliquots of bacteria were stored at −80° C.

Cultures of non-CF and CF airway epithelial cells were matched with regard to passage number, days in culture, and days at the air liquid interface. At least 24 h prior to the experiments, basolateral media of some cultures were supplemented with 100 µM KSCN. The apical surfaces of the cultures were washed with 0.25 ml PBS and the washes were pooled and stored at −20° C. $SCN^-$ dependent antibiotic activity was assayed using 560 µl of apical culture washes, adjusted to pH 5.7, and containing 2400-3600 *P. aeruginosa*. Since LPO was not secreted by the under these culture conditions, assays of washes also contained 1.125 µg/ml LPO and $10^{-5}$ M $H_2O_2$. Control experiments were performed using only PBS adjusted to pH 5.7. Growth of bacteria was not affected by addition of 1.125 µg/ml LPO, $10^{-5}$ M $H_2O_2$, or $5 \times 10^{-4}$ M $SCN^-$ singly or in pairs. However, addition of all three reconstituted a functional LPO system that was bactericidal. To show thiocyanate dependence, in some experiments CF culture secretions were also supplemented to $5 \times 10^{-4}$ M $SCN^-$. Mixtures were sampled immediately and 4 h after incubation at room temperature and CFU were determined by plating on LB Agar. Antibacterial activity was expressed as a ratio of CFU after 4 h to the starting CFU in the sample to control for slight differences in the starting number of bacteria.

LPO-dependent antibiotic activity of airway secretions obtained during surgery was determined using similar mixtures that were supplemented only with exogenous $10^{-5}$ $H_2O_2$ and not LPO or thiocyanate. LPO dependence of antibacterial activity in human airway secretions was demonstrated by its requirement for added $H_2O_2$ and sensitivity to $10^{-3}$ M dapsone in separate incubations.

To demonstrate that the LPO system has antibacterial functions in human airways, secretions were tested for their ability to prevent growth of bacteria in vitro. *P. aeruginosa*, that were diluted into PBS, pH 5.7, and incubated for 4 h at room temperature, increased in cell number by a factor of 2.1±0.3 (mean±SE) (n=6). Given the measured concentrations of LPO and $SCN^-$ in these secretions, existing $H_2O_2$ is expected to be consumed shortly after collection and thus no $H_2O_2$ was detectable (<$10^{-7}$ M) in the samples. It is unlikely that $H_2O_2$ would continue to be produced in secretions after collection since its source is thought to be cellular in origin. For this reason, secretions were supplemented with $10^{-5}$ M $H_2O_2$. Addition of $H_2O_2$ to $10^{-5}$ M or dapsone to $10^{-3}$ M had no measurable effect on cell growth (1.9±0.3, n=6). However when bacteria were diluted into airway secretions of six different patients in the presence of $10^{-5}$ M $H_2O_2$, cell growth was completely inhibited (0.98±0.16, n=6). Inclusion of dapsone, a potent inhibitor of LPO, significantly blocked the $H_2O_2$-dependent bacteriostatic properties of the airway secretions (1.68±0.31, n=6, p<0.05 compared to no dapsone). The $H_2O_2$ dependence and dapsone sensitivity of the bacteriostatic activity supports the conclusion that the LPO system functions in human airway as an antibacterial defense.

Example V

Thiocyanate Transport Defects and In Vitro Antibacterial Activity

To assess the effects of reduced $SCN^-$ transport on LPO-mediated antibacterial activity, the apical surfaces of cultures were washed with PBS and then the washes were used in LPO antibacterial assays. The day prior to washing, $SCN^-$ (100 µM) was added to the basolateral media to allow transport to the apical surface. Since culture conditions did not result in LPO synthesis and secretion, washes were supplemented with LPO. $H_2O_2$ was added to $10^{-5}$ M, a concentration that did not alone or with LPO, give rise to any antibacterial activity in washes from cells cultured in the absence of basolateral $SCN^-$. However, incubation of *P. aeruginosa* with LPO/$H_2O_2$ supplemented washes from non-CF cultures grown with basolateral $SCN^-$ resulted in LPO-dependent killing of bacteria. In contrast, incubation of *P. aeruginosa* under the same conditions with washes from CF cultures had no detectable LPO-dependent effect. Addition of exogenous $SCN^-$ (0.5 mM) to culture washes generated antibacterial activity in CF samples, demonstrating that the lack of antibacterial activity was the result of defective $SCN^-$ transport by the CF epithelial cells. Addition of the same amount of $SCN^-$ to the non-CF culture washes increased the LPO dependent activity in response to increased [$SCN^-$]. Thus, the lack of $SCN^-$ transport by CF cells compromised the in vitro LPO system reconstituted in apical washes of the ALI cultures.

Example VI

Airway LPO System Requires Continuous $H_2O_2$

To demonstrate that the airway LPO system requires continuous $H_2O_2$ production to function, LPO dependent killing was measured at pH 5.7, 6.2, and 6.8 using bovine milk LPO as a model for the airway LPO. Concentrations of the LPO system components were selected to be within the measured ranges in human airways. Bovine milk LPO (6.5 mg/ml), $SCN^-$ (0.4 mM) and $H_2O_2$ ($10^{-5}$ M) at all pH's tested effectively blocked the growth of *P. aeruginosa* and *Burkholderia cepacia* that frequently colonize cystic fibrosis airways. At pH 5.7 and 6.2, the activity was bactericidal, while at pH 6.8, it was bacteriostatic. Additional controls showed that the antibacterial activity was dependent on the presence of $SCN^-$ and $H_2O_2$. It was sensitive to heating the LPO to 100° C. prior to use and was inhibited by the peroxidase inhibitors dapsone ($10^{-3}$ M) or salicyl hydroxamic acid ($10^{-4}$ M). All of these characteristics were consistent with LPO-mediated antibacterial activity.

Since the pK of the LPO product HOSCN/$OSCN^-$ is about 5.3, the loss of bactericidal activity at higher pH could be due to the lower concentration of HOSCN. To increase the antibacterial product, the enzymatic consumption of $H_2O_2$ during experiments was compensated for at pH 6.8 by measuring the consumption of $H_2O_2$ at 0.5 h or 1 h intervals and replenishing to restore it to $10^{-5}$ M. Under these conditions the LPO system was bactericidal at pH 6.8 suggesting that replenishing $H_2O_2$ increased LPO activity required for bactericidal activity. Thus, it is expected that a constant supply of $H_2O_2$ in the airway for LPO's use results in an effective antibacterial system against *P. aeruginosa* and *B. cepacia*.

To demonstrate that human airway epithelia produce $H_2O_2$, enzymatic machinery was identified in these cells that produces $H_2O_2$ and $H_2O_2$ production by human airway epithelia re-differentiated in culture at an air-liquid interface was measured. Reverse transcription-polymerase chain reaction (RT-PCR) was performed with primers designed to detect any mammalian NADPH oxidase capable of producing $H_2O_2$ through superoxide intermediate. This RT-PCR yielded a cDNA fragment that when sequenced was 99% identical with human Dual Oxidase 1 (Duox1), the large molecular weight NADPH oxidase homologue. To further confirm these results, gene specific primers chosen within the 5' UTR and 3' UTR of homo sapiens Dual Oxidase 1 (Genbank accession No 017434) were used for RT-PCR and generated the complete 5.5 Kb cDNA sequence having 100% identity with human Duox1.

As expected from identification of Duox1 in the cells, $H_2O_2$ was produced at the apical surface of airway epithelial cells as detected using a quantitative fluorometric-micro-assay based on horseradish peroxidase catalyzed $H_2O_2$ oxidation of N-acetyl-3,7 dihydroxyphenoxazine. Previous studies on porcine thyroid plasma membrane preparations that contained Duox1 demonstrated that NADPH oxidase activity was calcium-dependent in these membranes. See Nakamura, et al. (1987) *J. Biochem.* (Tokyo) 102(5):1121-32). Since the predicted molecular structure of Duox1 and 2 identified an intracellular loop containing 2 EF-hand calcium-binding motifs, the $Ca^{2+}$ stimulated $H_2O_2$ production was assessed. ALI cultures were stimulated for one hour with Thapsigargin (1 µM), an inhibitor of the endoplasmic reticulum calcium ATPase pump that increases intracellular $Ca^{2+}$. Concomitant with the increment of the intracellular calcium concentration, the apical $H_2O_2$ produced by stimulated cells also increased from a baseline value of 59±16 $H_2O_2$ pmoles/hr to 128±17 $H_2O_2$ pmoles/hr, for control and thapsigargin, respectively. To confirm that this $H_2O_2$ production was due to a NADPH oxidase-like activity, the cells were treated with thapsigargin in the presence of 1 µM of Diphenyleneiodonium (DPI), a well known NADPH oxidase inhibitor that disrupts the activity of the flavoprotein oxidoreductase domain. In this assay, the cells were incubated for one hour with either DPI alone or in combination with thapsigargin (1 μM). These results demonstrated that the inhibitory effect of DPI blocked the thapsigargin induced increase in apical $H_2O_2$ production (45±19 $H_2O_2$ pmoles/hr). The demonstration of DPI inhibitable apical $H_2O_2$ generation under the control of cytosolic calcium concentration is consistent with the presence of Duox1 in airway epithelia. The data support the idea that stimulation of Duox1 produces $H_2O_2$ for the LPO mediated antibiotic activity.

All references cited herein are incorporated herein by reference to the same extent as if each individual publication or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An inhaler comprising a mouthpiece and containing a composition and adapted to deliver the composition as an aerosol to a lung of a person, wherein the composition comprises $H_2O_2$.

2. The inhaler of claim 1 wherein the composition further comprises thiocyanate.

3. The inhaler of claim 1 wherein the composition further comprises a peroxidase.

4. The inhaler of claim 1 wherein the composition further comprises an antibiotic.

5. The inhaler of claim 1 wherein the composition further comprises an anti-fungal or an antiviral.

6. The inhaler of claim 1 wherein the composition further comprises a sulfhydryl compound.

7. The inhaler of claim 1 wherein the composition further comprises a pharmaceutically acceptable carrier.

8. The inhaler of claim 2 wherein the composition further comprises a pharmaceutically acceptable carrier.

9. The inhaler of claim 3 wherein the composition further comprises a pharmaceutically acceptable carrier.

10. The inhaler of claim 4 wherein the composition further comprises a pharmaceutically acceptable carrier.

11. The inhaler of claim 5 wherein the composition further comprises a pharmaceutically acceptable carrier.

12. The inhaler of claim 6 wherein the composition further comprises a pharmaceutically acceptable carrier.

13. The inhaler of claim 1 further comprising a nozzle and an actuator.

14. The inhaler of claim 2 further comprising a nozzle and an actuator.

15. The inhaler of claim 3 further comprising a nozzle and an actuator.

16. The inhaler of claim 4 further comprising a nozzle and an actuator.

17. The inhaler of claim 5 further comprising a nozzle and an actuator.

18. The inhaler of claim 5 further comprising a nozzle and an actuator.

19. The inhaler of claim 7 further comprising a nozzle and an actuator.

20. The inhaler of claim 8 further comprising a nozzle and an actuator.

21. The inhaler of claim 9 further comprising a nozzle and an actuator.

22. The inhaler of claim 10 further comprising a nozzle and an actuator.

23. The inhaler of claim 11 further comprising a nozzle and an actuator.

24. The inhaler of claim 12 further comprising a nozzle and an actuator.

* * * * *